US00PP31474P2

(12) United States Plant Patent
Verschuren

(10) Patent No.: US PP31,474 P2
(45) Date of Patent: Feb. 25, 2020

(54) ***CUPRESSUS* PLANT NAMED 'HAVFREGO'**

(50) Latin Name: *Cupressus macrocarpa*
Varietal Denomination: Havfrego

(71) Applicant: Marcus Johannes Wilhelmus Maria Verschuren, Haps (NL)

(72) Inventor: Marcus Johannes Wilhelmus Maria Verschuren, Haps (NL)

( * ) Notice: Subject to any disclaimer, the term of this patent is extended or adjusted under 35 U.S.C. 154(b) by 0 days.

(21) Appl. No.: 16/350,626

(22) Filed: Dec. 11, 2018

(51) Int. Cl.
*A01H 7/00* (2006.01)

(52) U.S. Cl.
USPC ..... Plt./213

(58) Field of Classification Search
USPC ..... Plt./213

CPC ... A01H 7/00; A01H 5/00; A01H 5/04; A01H 5/02; A01H 5/025
See application file for complete search history.

(56) References Cited

PUBLICATIONS

Staatscourant Gazette Dec. 2016 Raad voor plantenrassen Nr 71341-n1, pp. 1 and 4. (Year: 2016).*
Vakouftsis et al. Effect of IBA, time of cutting collection, type of cuttings and rooting substrate on vegetative propagation in *Cupressus macrocarpa* 'Goldcrest', Propagation of Ornamental Plants 9(2): 65-70, 2009. (Year: 2009).*

* cited by examiner

*Primary Examiner* — June Hwu
(74) *Attorney, Agent, or Firm* — Penny J. Aguirre

(57) ABSTRACT

A new cultivar of *Cupressus* plant named 'Havfrego' that is characterized by its foliage that is uniquely colored; emerging green and changing to having white tips, and its upright plant habit.

2 Drawing Sheets

Botanical classification: *Cupressus macrocarpa.*
Varietal denomination: 'Havfrego'.

CROSS REFERENCE TO A RELATED APPLICATION

This application is related to a plant breeders' rights application filed in the Netherlands on Nov. 22, 2016, application No. CPS6. There have been no offers for sale anywhere in the world prior to the effective filing date of this Application and no accessibility to one of ordinary skill in the art could have been derived from the printed plant breeder's rights documents.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Cupressus macrocarpa* and will be referred to hereafter by its cultivar name, 'Havfrego'. 'Havfrego' is a new cultivar of Monterey cypress tree grown for landscape use.

The new *Cupressus* arose from a breeding program conducted by the Inventor in Haps, The Netherlands. The objective of the breeding program was to develop new cultivar of Cupressus with uniquely colored foliage.

The new cultivar arose from a cross made in 2008 between *Cupressus macrocarpa* 'Goldcrest' (not patented) and an unnamed seedling from the Inventor's breeding program as the male parent. The Inventor selected 'Havfrego' as a single unique plant in 2011.

Asexual propagation of the new cultivar was first accomplished by apical semi-hardwood cuttings by the Inventor in Haps, The Netherlands in October of 2015. Asexual propagation by apical semi-hardwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Havfrego', as a unique cultivar of *Cupressus.*

1. 'Havfrego' exhibits foliage that is uniquely colored; emerging green and changing to having white tips.
2. 'Havfrego' exhibits an upright plant habit.

The female parent plant, 'Goldcrest', differs from 'Havfrego' in having foliage with golden colored foliage. The male parent differs in having foliage that is green in color. 'Havfrego' can be compared to the cultivar 'Wilma' (syn. 'Wilma Goldcrest', not patented).

'Wilma' is similar to 'Havfrego' in having a foliage that is uniquely colored and in having an upright plant habit. 'Wilma' differs from 'Havfrego' in having lacking white foliage and in having a more a narrow columnar plant habit.

BRIEF DESCRIPTION OF THE DRAWINGS

The accompanying colored photographs illustrate the overall appearance and distinct characteristics of the new

*Cupressus*. The photographs were taken of a 36-month-old plant as grown in a conventional greenhouse in a 16-cm container in Haps, The Netherlands.

Figure 1:
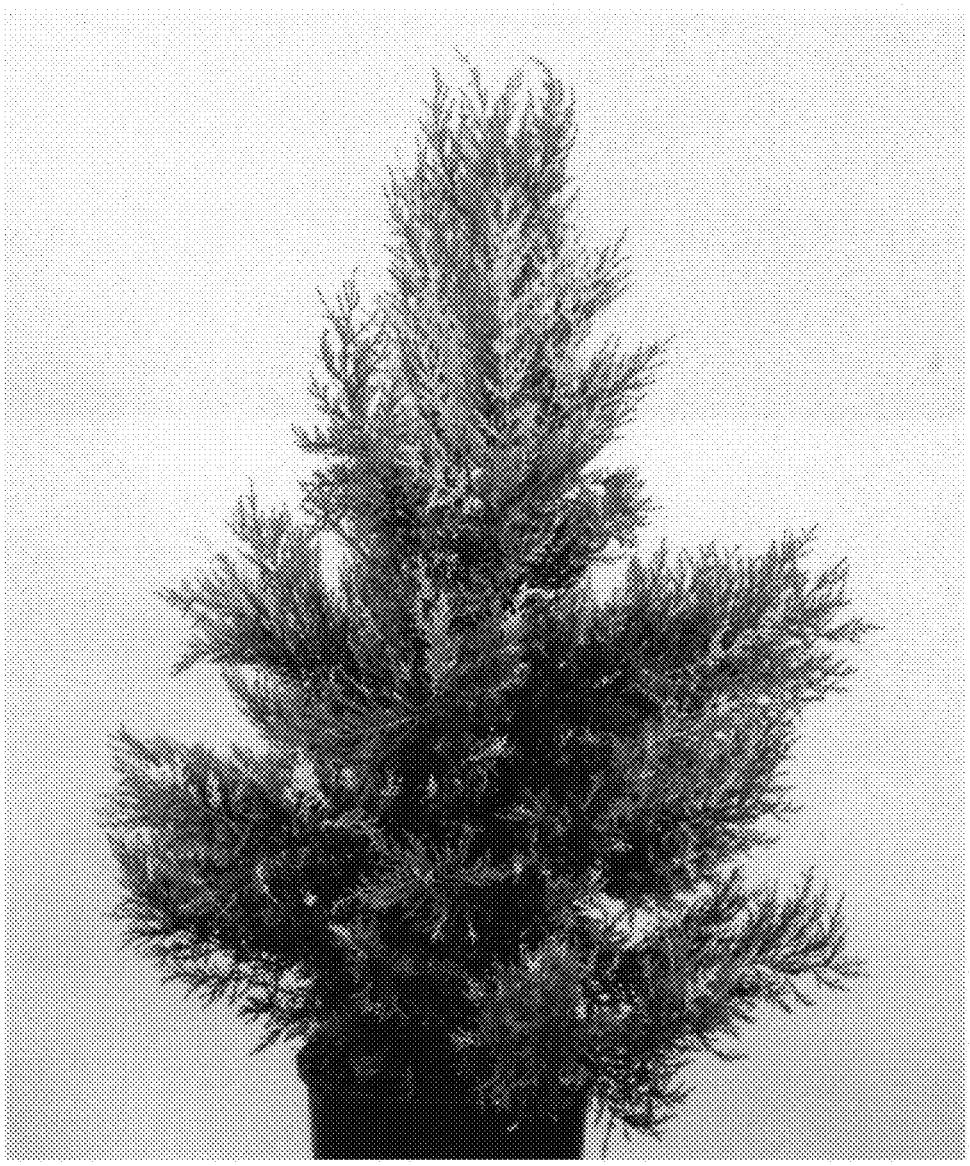

The photograph in FIG. 1 provides an overall view of the plant habit of 'Havfrego'.

Figure 2:
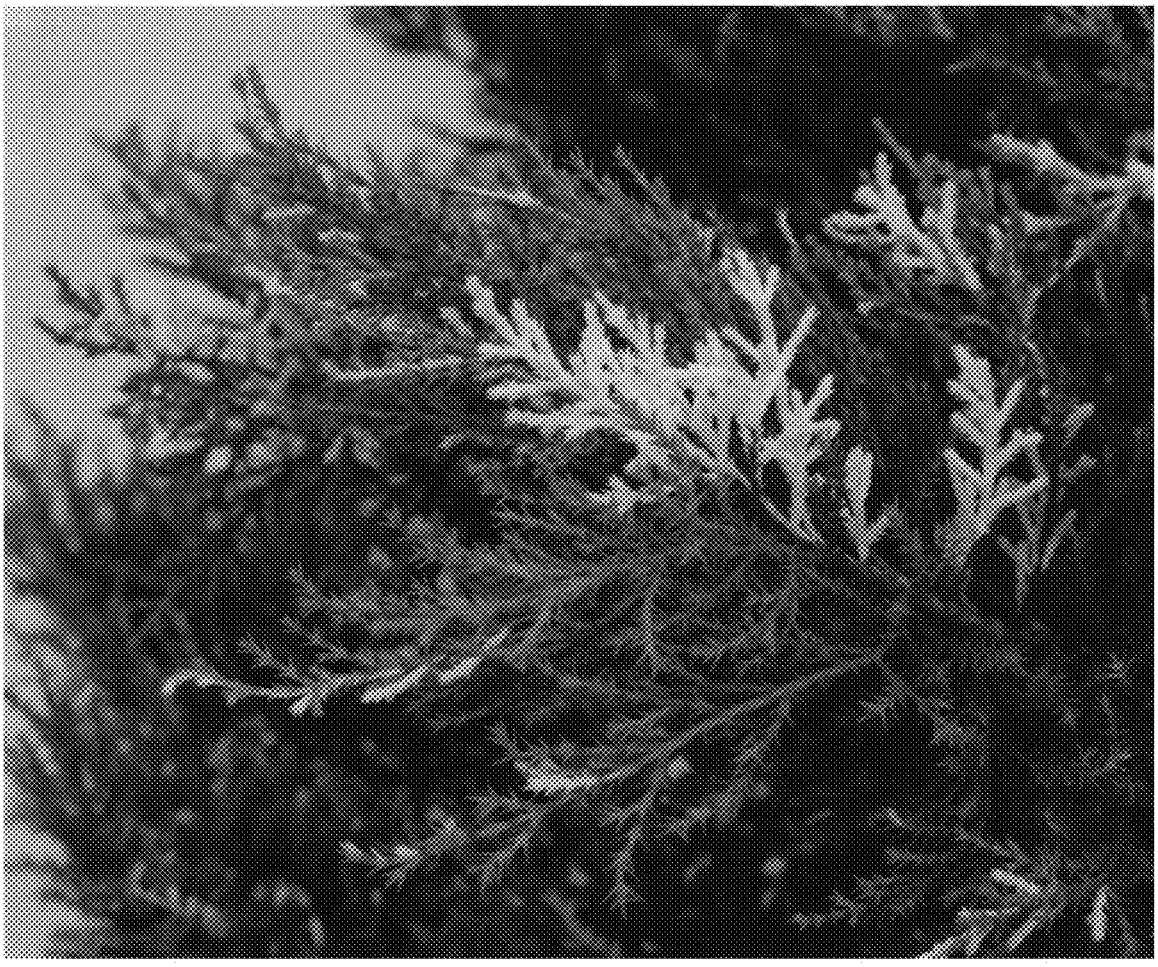

The photograph in FIG. 2 provides a close-up view of the foliage of 'Havfrego'.

The colors in the photographs are as close as possible with the photographic and printing technology utilized and the values cited in the detailed botanical description accurately describe the colors of the new cultivar.

DETAILED BOTANICAL DESCRIPTION

The following is a detailed description of 24-month-old plants of the new cultivar as grown in 16-cm containers in Haps, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Coniferous evergreen tree.

*Growth habit.*—Upright.

*Height and spread.*—An average of 60 cm in height and 40 cm in width.

*Cold hardiness.*—At least in U.S.D.A. Zone 10.

*Diseases and pests.*—Not more susceptible or resistant to pests and diseases than other *Cupressus*.

*Root description.*—Fibrous and well-branched.

*Growth rate.*—Moderate.

*Propagation.*—Root cuttings.

*Root development.*—Roots initiate in 3 to 4 weeks and will fully develop in a 11-cm container in about 16 months.

Branch description:

*Branching.*—Very freely branching, average of 1 main branch 74 lateral branches, held in multiple angles, average of 75°.

*Branch surface* (*texture*).—All branches covered with scale-like leaves with upper surface of leaf scalesvery slightly glossy, trunk surface is coarsely fibrous.

*Branch shape.*—Rounded.

*Branch size.*—Trunk; an average of 35 cm in height and 1.5 cm in width at the soil line, lateral branches; an average of 23.3 cm in length and 3 mm in diameter.

*Internode length.*—Average of 1.2 cm.

*Branch color.*—Young; with green leaves 144C, with white leaves 157B, mature and internodes; 143B to 143C or 145D to 158D and 193A, older bark on trunk 166B and 200B to 200C.

*Branch strength.*—Strong.

Foliage description:

*Leaf arrangement.*—Opposite.

*Leaf shape.*—Lanceolate, involute from margin of needle-like tips.

*Leaf aspect.*—Base of leaves adpressed to branch (scale-like), needle-like tips held at an average angle 35°.

*Leaf division.*—Simple.

*Leaf base.*—Decurrent.

*Leaf apex.*—Apiculate.

*Leaf venation.*—Not visible.

*Leaf margins.*—Entire.

*Leaf surface.*—Both surfaces smooth and slightly glossy with abaxial surface lacking glands and pits.

*Leaf color.*—Young upper and lower surface; 144C with many of the growing tips becoming 157B, mature upper and lower surface; 143B to 143C or 145D to 158D and 193A

*Leaf fragrance.*—When crushed, the leaves spread a pleasant fragrance, typical for *Cupressus macrocarpa*.

*Leaf size.*—An average of 3.5 mm in length and 1.5 mm in width.

*Leaf quantity.*—Over 4,500 scale-like leaves per lateral branch.

*Durability to stresses.*—High.

Cone description: No cones have been produced to date.

It is claimed:

1. A new and distinct cultivar of *Cupressus* plant named 'Havfrego' as herein illustrated and described.

* * * * *